United States Patent [19]

Masamune et al.

[11] 4,405,802
[45] Sep. 20, 1983

[54] CHIRAL BORON ENOLATE REAGENTS

[75] Inventors: Satoru Masamune, Newton; William Choy, Boston, both of Mass.

[73] Assignee: Massachusetts Institute of Technology, Cambridge, Mass.

[21] Appl. No.: 350,854

[22] Filed: Feb. 22, 1982

[51] Int. Cl.$^3$ .......................... C07F 5/02; C07F 5/04; C07F 5/05; C07F 7/08

[52] U.S. Cl. .................................. 556/402; 556/403; 562/579

[58] Field of Search ................. 556/402, 403; 562/579

[56] References Cited

U.S. PATENT DOCUMENTS

| | | | |
|---|---|---|---|
| 2,831,009 | 4/1958 | Seyforth | 556/402 |
| 3,154,520 | 10/1964 | Dupont et al. | 556/402 X |
| 3,519,670 | 7/1970 | Markovitz | 556/403 X |
| 3,567,410 | 3/1971 | Young | 556/403 X |

*Primary Examiner*—Paul F. Shaver
*Attorney, Agent, or Firm*—Arthur A. Smith, Jr.; Paul J. Cook

[57] ABSTRACT

Chiral boron enolates are provided having the formulae:

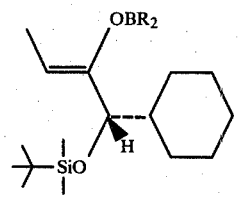

Formula I

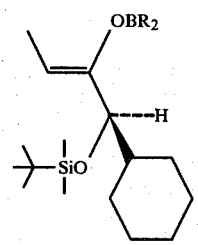

Formula II wherein $R_2B$ is 9-borobicyclo[3.3.1]non-9-yl(BBN) or R is n-butyl, cyclopentyl, or another alkyl group.

The boron enolates can be condensed with aldehydes to produce aldol stereospecific product which includes a β-hydroxy-α-methyl carbonyl unit in the product structure.

8 Claims, No Drawings

CHIRAL BORON ENOLATE REAGENTS

BACKGROUND OF THE INVENTION

The Government has rights in this invention under Contract No. NIH-5-R01-A1-15403-2 from the National Institute of Health and under IPA-0010.

This invention relates to novel chiral boron enolate reagents, their method of preparation and their use in performing stereospecific aldol condensation which, after simple operations, yields enantiomerically pure β-hydroxycarboxylic acids.

The chemistry of macrolide antibiotics originated with the isolation of pikromycin. Soon afterward Streptomyces organisms yielded several other antibiotics which appeared to be chemically and antimicrobially related to pikromycin. By chemical degradations of these antibiotics, the gross structures of methymycin, erythromycin A and B, and carbomycin A (magnamycin), have been shown that each of them contains a lactone incorporated in a medium- or large-ring system. As the number of lactonic natural products has increased to well over one hundred, the word, "macrolide", originally restricted to the above antibiotics has gradually been used in a broader sense and in some cases overextended to cover even a macrocyclic lactam of plant origin. Structural, stereochemical and conformational studies of representative members of this steadily growing family have been actively pursued for the past two decades mainly by means of X-ray crystallographic, $^1$H- and $^{13}$C-NMR, and mass spectroscopic techniques.

In contrast to a plethora of structural studies that have appeared in the past 30 years, it is only in recent years that major synthetic accomplishments in the field of macrolides have been made. In the last decade, expertise in organic synthesis has already proved to be highly sophisticated, and general approaches, at least in principle, for syntheses of a vast number of important groups of compounds such as steroids, terpenes and alkaloids, were available. In the field of antibiotics, total syntheses of penicillins and cephalosporins and tetracylins had already been completed by the end of the sixties. Thus, the macrolides were the only remaining major family of antibiotics which presented a challenge to synthetic organic chemists. At least two major, general problems have been associated with the macrolide synthesis: one was the construction of a medium- or large-size lactone and the other involved the introduction of chiral centers into a straight chain aliphatic acid-say-through a stereospecific aldol condensation or acylation. There was a need to devise new synthetic methods for both problems. The first problem now has acceptable solutions, which have made possible the first total syntheses of methymycin, erythronolide A and B, tylonolide, carbomycin B, and many others. The second problem presents much to be further investigated.

The aglycones of the macrolide antibiotics are mainly of polypropionate origin, and the fundamental structural unit of these compounds is the 3-hydroxy-2-methyl carbonyl system, constituting the framework of these molecules. Therefore, it would be highly desirable to provide a methodology to synthesize in an enantioselective manner the syn isomers of 3-hydroxy-2-methyl carbonyl compounds (isomers with substituents extending on the same side of the main chain of the compound). Modification of this methodology would yield the corresponding anti isomers (isomers with substituents extending from opposite sides of the main chain of the compound). Thus, the enantioselective construction of the syn-3-hydroxy-2-methyl system would constitute a basic requisite for the stereoselective synthesis of macrolide antibiotics.

SUMMARY OF THE INVENTION

In accordance with this invention, chiral boron Z-enolates are provided having the formulae:

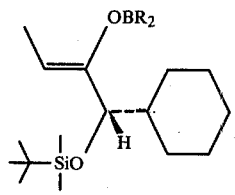

Formula I

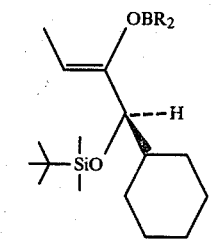

Formula II wherein $R_2B$ is 9-borobicyclo[3.3.1]non-9-yl(BBN), or R is n-butyl, cyclopentyl, or other alkyl groups.

The Z-enolates are capable of effecting the stereospecific condensation with aldehydes to form an aldol product capable of being converted to a product containing the syn-3-hydroxy-2-methyl carbonyl moiety without producing the corresponding anti-isomer. The enolates are produced by hydrogenating S or R-mandelic acid and converting the resulting hexahydro derivative to the corresponding ethyl ketone utilizing ethyllithium in ether. The ketone then is silylated, and finally the silyated product is reacted with a dialkyl boron triflate in the presence of diisopropylethylamine or another hindered tertiary amine. The chiral boron enolate then is suitable for aldol condensation with an aldehyde yielding a product containing the optically active syn-3-hydroxy-2-methyl carbonyl moiety.

DESCRIPTION OF SPECIFIC EMBODIMENTS

The compounds of this invention are prepared by a multi-step process. In the first step, optically pure S- or R-mandelic acid is hydrogenated to form the corresponding hexahydro derivative in the presence of a hydrogenation catalyst, such as platinum, palladium, rhodium or the like. The hydrogenation is effected following a literature procedure. The resulting hexahydro derivative then is converted to the corresponding ethyl ketone by a reaction with an alkyl lithium such as ethyllithium in a suitable solvent such as diethyl ether, usually at a temperature between about −78° C. and 0° C. The ketone product then is recovered by distillation or chromatography.

The ketone product then is silylated by reaction with tert-butyldimethylsilyl chloride with imidazole in tetrahydrofuran or tert-butyldimethylsilyl trifluoromethanesulfonate with pyridine in methylene chloride.

In the final step, the compounds of this invention are prepared by reacting the silylated product with a dialkylboron trifluoromethanesulfonate at a temperature between about −78° C. and about 0° C., in an oxygen free, moisture free atmosphere such as nitrogen, argon or the like, and in the presence of a tertiary amine such as diisopropylethylamine, lutidine, syn-collidine, 2,6-di-tert-butyl-4-methyl pyridine. The tertiary amine functions to neutralize the trifluoromethanesulfonic acid produced. The reaction also is conducted in the presence of an inert solvent such as dichloro methane, hexane, or diethyl ether. The chiral boron enolate product of this invention then is used in the final process step to produce the products of this invention represented as follows:

Equation 1
Scheme 1

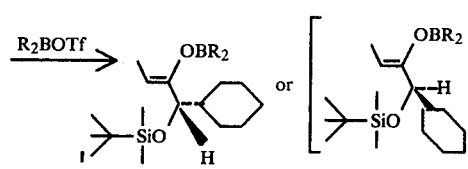

1a: BR₂ = 9-BBN    2a: BR₂ = 9-BBN
1b: R = n-C₄H₉    2b: R = n-C₄H₉
1c: R = c-C₅H₁₁    2c: R = c-C₅H₁₁

BBN: 9-borabicyclo[3.3.1]non-yl

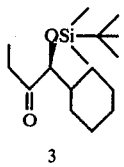

3

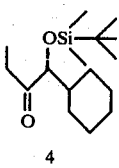

4

In Equation I, BR₂ and R are described above.

The aldol condensation process utilizing the compounds of this invention are set forth in Equation 2.

Equation 2

R—CHO + 1a, 1b or 1c 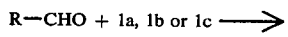

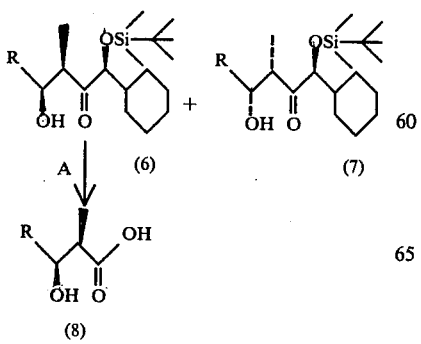

-continued
Equation 2

A:
(1) conc HF—CH₃CN (1:20 v/v) Room Temperature, 3.5 h.
(2) NaIO₄(CH₃OH/H₂O) Room Temperature, 3 h.

The condensation products are converted into the corresponding β-hydroxy-αmethylcarboxylic acid first by reaction with conc. hydrogen fluoride in acetonitrile and then by reaction with meta-sodium periodate in a suitable solvent such as methanol-water mixture, ethanol-water mixture or dioxane-water mixture. The acidic product then is recovered by extraction.

The following examples illustrate the present invention and are not intended to limit the same.

EXAMPLE I

Optically pure S- or R-mandelic acids obtained from Aldrich Chemical Co. was hydrogenated with Rh/Al₂O₃ under the usual conditions to yield the corresponding hexahydro derivative. The hexahydro derivatives were reacted with 3.5 equiv. of ethyllithium (ether, −78° C.→0° C.) provided a 75% yield of the corresponding ethyl ketones which were in turn silylated to afford under the following conditions: tert-butyldimethylsilyl chloride and imidazole in refluxing tetrahydrofuran. Generation of boron enolates 1a-c (or 2a-c) from 3 (or 4) and subsequent aldol condensation with a variety of aldehydes 5 are standardized and were performed as follows: To a CH₂Cl₂ (5 ml) solution of 3 (1.0 mmol) was added at −78° C., under nitrogen, diisopropylethylamine (1.0 mmol) and then a dialkylboron trifluoromethanesulfonate (0.9 mmol). After stirring for 1 h and 45 min at 0°, an aldehyde (0.5 mmol) was added dropwise and the resulting mixture was stirred an additional 45 min. The usual workup, including preparative TLC, provided a mixture of diastereomeric isomers, 6 and 7, uniformly in 70–85% isolated yield based on the aldehyde. The major isomer which constituted at minimum 93% of the product mixture, was further converted quantitatively into the corresponding 3-hydroxy-2-methylcarboxylic acid 8 via two steps: desilylation and sodium metaperiodate oxidation. The structure and absolute configuration of 8 was established by comparison with that derived from a compound of known stereochemistry in each case.

TABLE I

Results of the Aldol Condensations of Achiral Aldehydes with Dialkylboron Enolates (1a-c)

| Aldehyde (5) | Boron Enolate | Ratio of 6 to 7 | Major β-hydroxyacid (8) |
|---|---|---|---|
| HCHO 5a | 1c | >100:1 | 8a |
| C₆H₅—CHO 5b | 1a<br>1b<br>1c | 14:1<br>40:1<br>75:1 | 8b |
| 5c ⋀CHO | 1a<br>1b<br>1c | 17:1<br>50:1<br>>100:1 | 8c |

TABLE I-continued
Results of the Aldol Condensations of Achiral
Aldehydes with Dialkylboron Enolates (1a-c)

| Aldehyde (5) | Boron Enolate | Ratio of 6 to 7 | Major β-hydroxyacid (8) |
|---|---|---|---|
| 5d C₆H₅–O–CH=CH–CHO | 1a<br>1b<br>1c | 16:1<br>28:1<br>100:1 | 8d |
| 5e (CH₃)₂CH–CHO | 1a<br>1b<br>1c | >100:1<br>>100:1<br>no reaction | 8e |

(a)The product ratios are based mainly on the relative intensitives of several sets of the corresponding signals observed in the 250 MHz ¹H NMR spectrum of each diastereomeric mixture.

Table I summarizes the results of the aldol condensations with three different boron enolates 1a, b and c, carrying the 9-borabicyclo 3.3.1 non-9-yl (9-BBN), di-n-butyl, and dicyclopentyl ligands, respectively. Several notable features are evident. (1) In all cases the aldo products consist of 2,3-syn products 6 and 7 and no trace of the corresponding 2,3-anti-isomers is found to the limit of our analytical methods. In view of the earlier findings, this indicates the exclusive formation of Z-enolates as shown in 1a-c. (2) The ratios of 6 and 7 are impressively high and increase with the size of the ligands attached to the boron. With the dicyclopentyl-boron enolate 1c, both benzaldehyde and the two other aldehydes with no substituents at the α-position provide a single aldol product, virtually free from its diastereoisomer. In the case of the α-branches aldehyde, excellent stereoselection is already achieved with the less bulky reagents 1a and 1b, but the fact that the reaction does not proceed with 1c is very likely due to steric congestion in the transition state. (3) The absolute configurations of the two chiral centers present in each of the β-hydroxyacid products are determined as shown in the Table, and are experimentally correlated with the stereochemistry of the ethyl ketone. The use of 2 instead of 1 obviously leads to the formation of the enantioners of 8 and thus the diastereoselective synthesis of 6 followed by oxidative cleavage of the -hydrosy-keto group constitutes an enantio-selective synthesis of β-hydrosy-α-methylcarboxylic acids. Many natural product syntheses potentially utilize these compounds as starting materials, which are now available in optically active form with ease and in quantity. We recommend the use of 1a for aldehydes with an α-substituent and that of 1c for aldehydes carrying no α-substituent.

Although the stereochemical course of the aldol reaction is extremely complicated, the commonly accepted 6π electron chair-type transition state may serve to rationalize at least tentatively, the high selectivity described above. In the transition states T_S and T_R

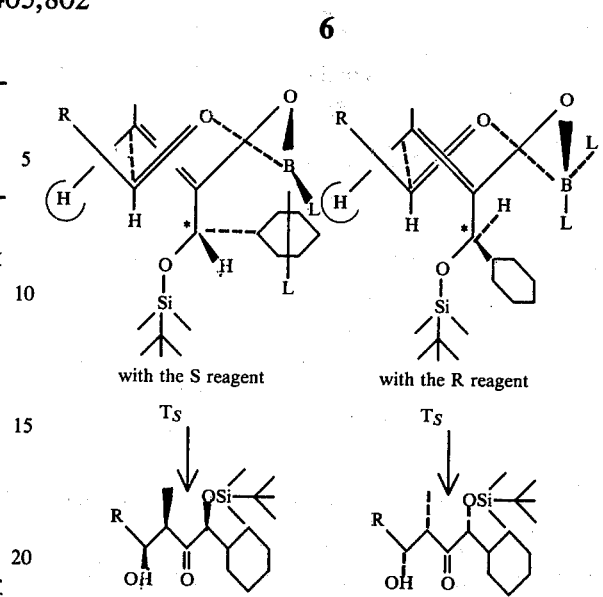

with the S reagent     with the R reagent proposed for the reaction of 1(a-c) and 2(a-c) with an aldehyde, the substituents attached to the chiral center of the enolate reagent are so oriented as to minimize the steric congestion. The interactions of cyclohexyl moiety with the vinylic hydrogen and the ligands attached to boron are avoided as shown in T_S and T_R. Thus, the stereochemistry of the chiral center dictates the approach of the enolate with respect to the aldehyde [approach from α face of the aldehyde as depicted in T_S, from the β face as shown in T_R] which is translated into the absolute configuration of the final aldo product.

Reaction of 1(a-c) or 2(a-c) with a chiral aldehyde is of great interest. The high diastereoselectivity of a chiral enolate can outweigh many other factors (such as the Cram/anti-Cram selectivity of the aldehyde which influence the enolate approach to the aldehyde. As a consequence, the stereochemistry at both the 2 and 3 positions of compounds:

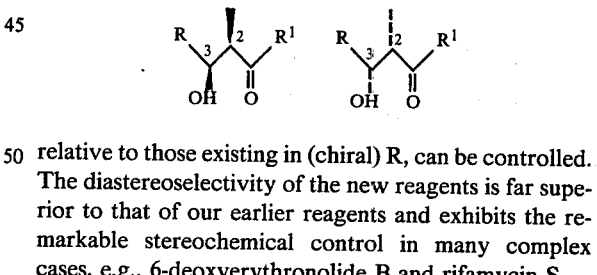

relative to those existing in (chiral) R, can be controlled. The diastereoselectivity of the new reagents is far superior to that of our earlier reagents and exhibits the remarkable stereochemical control in many complex cases, e.g., 6-deoxyerythronolide B and rifamycin S.

We claim:

1. The compound of the formula selected from the group consisting of:

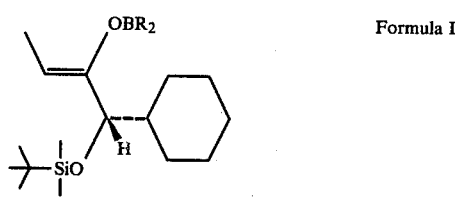

Formula I

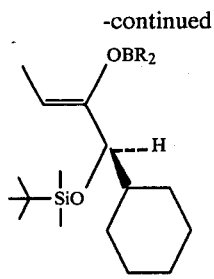

Formula II wherein R is selected from the group consisting of n-butyl and cyclopentyl or R$_2$B is 9-borobicyclo[3.3.1]non-9-yl.

2. The compound of claim 1 represented by Formula I.

3. The compound of claim 1 represented by Formula II.

4. The compound of claim 1 wherein BR$_2$ is 9-borobicyclo[3.3.1]non-9-yl.

5. The compound of claim 1 wherein R is n-butyl.

6. The compound of claim 1 wherein R is cyclopentyl.

7. The process for forming the compound of claim 1 which comprises reacting a compound selected from the group consisting of:

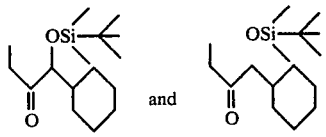

with a dialkylboron trifluoromethanesulfonate wherein the dialkylboron portion is selected from the group consisting of di-n-butyl boron, dicyclopentyl boron and 9-borobicyclo[3.3.1]non-9-yl.

8. The process for effecting aldol condensation which comprises reacting an aldehyde with a compound of claim 1 to form a silylated product and desilylating said silylated product followed by oxidative cleavage under conditions to form a compound having the formula selected from the group consisting of:

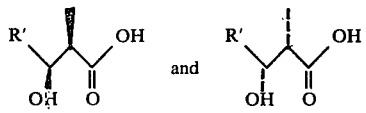

wherein R' is aliphatic or aromatic.